United States Patent [19]

Singh et al.

[11] 4,235,969

[45] Nov. 25, 1980

[54] PROCAINAMIDE ANTIGEN CONJUGATES AND ANTIBODIES

[75] Inventors: Prithipal Singh, Santa Clara; Marcel R. Pirio, Mountain View, both of Calif.

[73] Assignee: Syva Company, Palo Alto, Calif.

[21] Appl. No.: 903,420

[22] Filed: May 8, 1978

[51] Int. Cl.$^2$ .......................... C07G 7/00; C07G 7/02
[52] U.S. Cl. ................................ 435/188; 23/230 B; 260/112 B; 260/112 R; 260/121; 424/85; 424/88; 435/7; 435/190; 562/426; 562/448; 562/450
[58] Field of Search ...................... 195/63; 424/85, 88; 260/112 R, 112 B, 121; 435/188, 7, 190

[56] References Cited

U.S. PATENT DOCUMENTS

| | | | |
|---|---|---|---|
| 3,817,837 | 6/1974 | Rubenstein et al. | 195/63 X |
| 3,843,696 | 10/1974 | Wagner et al. | 260/112 R X |
| 3,875,011 | 4/1975 | Rubenstein et al. | 195/103.5 R |
| 3,888,866 | 6/1975 | Leute et al. | 424/85 X |
| 4,046,722 | 9/1977 | Rowland | 260/112 R X |
| 4,065,354 | 12/1977 | Ullman et al. | 195/63 |
| 4,069,105 | 1/1978 | Singh | 424/88 X |

OTHER PUBLICATIONS

Clin. Chem. 23, pp. 705–708, (1977), Rocco et al.
Clin. Exp. Immunol. (1968), 3, pp. 901–909, Russell et al.
Dictionary of Organic Compounds, 4th Ed., vol. 5, p. 2778, 1965.

*Primary Examiner*—Howard E. Schain
*Attorney, Agent, or Firm*—Bertram I. Rowland

[57] ABSTRACT

Compounds are provided for use in the preparation of reagents which can be used in immunoassays for the determination of benzamides of N,N-dialkylethyleneamines. A linking group is provided, at a particular site of the drug, which provides a link between the above compounds and an antigen, with the resulting conjugate being employed for the preparation of antibodies. The antibodies find particular use in competitive protein binding assays. Conjugates to enzymes are prepared which find particular use in homogeneous enzyme immunoassays.

12 Claims, No Drawings

PROCAINAMIDE ANTIGEN CONJUGATES AND ANTIBODIES

BACKGROUND OF THE INVENTION

1. Field of the Invention

There is increasing concern with the manner in which drugs are administered since both the manner and amount of the drug which is administered, affects the blood level of the drug during an extended period of time and in many instances, the effectiveness of the drug is directly related to the concentration of the drug in the bloodstream. The rate at which the desired blood level is achieved or exceeded will depend upon the nature of the drug, the manner of administration, the dosage, as well as the rate of metabolism. The rate at which a drug will enter the bloodstream when administered other than intravenously and the rate at which the drug is metabolized varies widely with individuals. Furthermore, the level of effectiveness will also vary widely with individuals.

It is therefore desirable when administering drugs to ascertain the individual's level of effectiveness, the rate at which this level is achieved at a particular dosage and the time for which the level is maintained. In this manner, the amount of drug which is administered can then be carefully monitored to maintain the desired level. In this way, effectiveness can be assured and side effects minimized.

In order to monitor a drug in a physiological fluid, it is necessary to have sensitive tests which enable the rapid determination of the drug as distinct from any ineffectual metabolites. Thus, the test must clearly distinguish between the drug of interest and compounds of very similar structure. In competitive protein binding assays, antibodies are employed which are prepared by means of antigenic conjugates of derivatives of the drug of interest. In order for the antibodies to be effective, they must be produced in high titer, have a strong binding constant to the drug of interest, and weakly bind to compounds of similar structure.

With many drugs, there may be closely analogous compounds which may be administered which have different activity or may be metabolized to other compounds of different activity. In these situations, it is necessary to distinguish between the compound which is administered and its metabolite, so that the individual concentrations of each of the drugs in the bloodstream can be determined and monitored.

There is also a need for a reagent which provides a measurable signal related to the amount of drug present in the assay medium. Where antibodies are involved, the reagent must effectively compete with the drug for antibody binding in a reproducible manner and provide for significant changes in the signal with small changes in the drug concentration over the concentration range of interest.

Other considerations for a reagent are that it is not affected by materials present in the unknown sample to be assayed or that materials which do interfere may be removed from the sample. Additionally, a reagent should provide an easily determinable signal, should be stable under the assay conditions, should have a good storage life and should be readily recognized by the antibodies for the drug.

2. Brief Description of the Prior Art

Descriptions of competitive protein binding assays may be found in U.S. Pat. Nos. 3,817,837, 3,850,752, 3,690,834, and in an article by Murphy, 27 J. Clin. Endocr. 973(1967). Preparation of antigenic conjugates and antibodies for a number of different drugs may be found in U.S. Pat. Nos. 3,888,866, 3,766,162, 3,843,696 and 3,878,178. U.S. Pat. No. 3,875,011 discloses glucose-6-phosphate dehydrogenase conjugates for use in homogeneous enzyme immunoassays.

Articles concerned with antibodies to procainamide and its derivative include Russell and Ziff, Clin. Exp. Immunol (1968) 3, 901 and Rous et al, Clin. Chem. (1977), 23, 705.

SUMMARY OF THE INVENTION

Functionalized derivatives of drugs comprising substituted benzamides of N,N-dialkyl alkyleneamines are provided for conjugation to antigens or enzymes. The antigenic conjugates are employed for the preparation of antibodies, which in combination with the enzyme conjugates, find use in homogeneous enzyme immunoassays. The particular enzyme conjugates are employed for the detection or procainamide or its N-acetyl derivative (N-acetyl procainamide). The reagents can be employed for monitoring individually the blood levels of both N-acetyl procainamide and procainamide.

DESCRIPTION OF THE SPECIFIC EMBODIMENTS

Novel compositions are provided which are derivatized benzamides of N,N-dialkyl alkylenediamines, whereby one of the N-alkyl groups is replaced with a nonoxocarbonyl-alkyl substituent. The benzamide is substituted at an annular carbon atom with an amino group or acetylamino group at the para position. The nonoxocarbonyl functionally (including the nitrogen analog) is employed for conjugation to antigens, usually poly(amino acids) or polysaccharides, and enzymes. The antigenic conjugate is employed for the preparation of antibodies, which in combination with the enzyme conjugate can be used in sensitive homogeneous enzyme immunoassays for the detection of procainamide or N-acetyl procainamide. The linking group will normally have at least 1 carbon atom and not more than about 8 carbon atoms, preferably having from about 2 to 4 carbon atoms and more preferably 3 carbon atoms.

The antigenic conjugates provide antibodies which are capable of selection of procainamide or N-acetyl procainamide. That is, the antibodies when used in an immunoassay have low cross-reactivity to organic compounds of similar structure other than the compound of interest and are able to strongly bind selectively.

For the most part, the compositions of this invention will have the following formula:

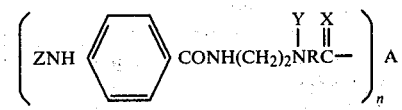

wherein:

Z is hydrogen or acetyl;

Y is alkyl of from 1 to 3 carbon atoms, normally 2 carbon atoms i.e. ethyl;

X is oxygen or imino (NH);

R is a linking group of from 1 to 8 carbon atoms having from 0 to 4 heteroatoms, which are oxygen, nitrogen and sulfur, wherein the oxygen is present as oxy or nonoxocarbonyl, particularly the latter, nitrogen is present as tertiary amino, amido or imino and sulfur is present as thioether or thiono, and having from 0 to 1 site of ethylenic unsaturation, as the only unsaturation, and is preferably of from 1 to 5 carbon atoms, more usually from 1 to 3 carbon atoms and alkylene.

A is hydroxyl, or an antigen or enzyme. When A is an antigen or enzyme, it is usually a poly(amino acid) of at least about 5,000 molecular weight, having no upper molecular weight, but normally being not more than 10,000,000, more usually not more than about 600,000. There will usually be different molecular weight ranges depending upon whether an antigen or an enzyme is involved, with enzymes generally ranging from about 10,000 to 600,000 molecular weight, more usually 10,000 to 300,000 molecular weight and antigens ranging from about 5,000 to $10^7$, usually from 20,000 to 600,000, and more usually from about 25,000 to 250,000 molecular weight; and n is 1 when A is hydroxyl. Otherwise, n is at least 1 and not more than the number of available amino groups present in A, generally being on the average in the range of about 1 to the molecular weight of A divided by 1,000, usually 1,500. For enzymes, n will be in the range of about 1 to 30, more usually in the range of 2 to 30, and preferably in the range of about 2 to 12, while for antigens the range will generally be from about 1 to 500, and preferably about 2 to 100, more preferably about 2 to 50, particularly with the middle molecular weight antigens.

The poly(amino acid) antigens and enzymes will for the most part have amino functionalities to which the nonoxocarbonyl (including the nitrogen analog) are linked to form amide and amidine linkages. To form amide linkages, mixed anhydrides, particularly monoalkyl carbonate esters, carbodiimides or active esters e.g. N-hydroxy succinimide or p-nitrophenyl, may be employed for activating the carboxyl group. For amidine formation, alkyl imidates are satisfactory. For polysaccharides, linkage will be at hydroxyl groups and the same carboxyl activators may be employed for formation of esters. Poly(amino acids) are preferred.

For the most part, the preferred compounds will have the following formula:

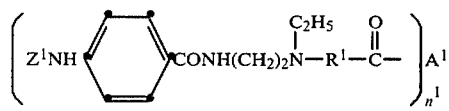

wherein:

$Z^1$ is hydrogen or acetyl;

$R^1$ is alkylene of from 1 to 4 carbon atoms, preferably of from 2 to 3 carbon atoms, and more preferably straight chain alkylene;

$A^1$ is hydroxyl, or a poly(amino acid), which is antigenic or an enzyme; when antigenic $A^1$ will be of from 5,000 to 600,000 molecular weight, preferably of from 20,000 to 300,000 molecular weight, when an enzyme, $A^1$ will be of from about 10,000 to 300,000 molecular weight, more usually of from about 10,000 to 150,000 molecular weight; and $n^1$ will be 1 when $A^1$ is hydroxyl; otherwise, $n^1$ will be on the average from 1 to the molecular weight of $A^1$ divided by 1,000, more usually from 1 to the molecular weight of $A^1$ divided by 1,500; When $A^1$ is an antigen, $n^1$ will generally be from about 2 to 100, more usually from about 10 to 60; when $A^1$ is an enzyme, $n^1$ will be on the average from about 1 to 20, more usually from about 2 to 16 and preferably from about 2 to 12.

Illustrative groups for R and $R^1$ are methylene, ethylene, propylene, methylethylene, butylene, hexylene, 3-aza-4-oxopentylene, and 2-butenylene.

The antigenic poly(amino acid) which may be used will vary widely as to molecular weight and nature of the poly(amino acid). The amino groups which provide the sites for linking will generally be present as terminal amino groups, as well as present in lysine, arginine, and histidine.

Various protein types may be employed as the antigenic material. These types include albumins, serum proteins, e.g. globulins, ocular lens proteins, lipoproteins, etc. Illustrative proteins include bovine serum albumin, keyhole limpet hemocyanin, egg ovalbumin, bovine gamma globulin, etc. Alternatively, synthetic poly(amino acids) may be prepared having a sufficient number of available amino groups e.g. lysines.

It is particularly useful for A or $A^1$ to be an enzyme which will act as a detector in an immunoassay system, although enzymes will function as antigenic material as well.

For use in an immunoassay, a number of characteristics of the enzyme can be considered e.g., substrates, cofactors, specificity, ubiquitousness, stability to temperature, pH optimum, turnover rate, and the like. Additional factors to be considered are the commerical availability of the enzyme, and the existence of already-developed reproducible assays.

In particular, for the purposes of this invention, the enzymes should either be capable of specific labelling or allow for efficient substitution, so as to be useful in the subject assays. By specific labelling is intended selective labelling at a site in relationship to the active site of the enzyme, so that upon binding of the antibody to the enzyme conjugate, the enzyme is satisfactorily inhibited. (By active site is intended those functionalities which are involved in the binding and transformation of the substrate(s) including cofactors). By sufficient substitution to be useful in the subject assay is intended that the enzyme be inhibited sufficiently when the enzyme conjugate is bound to the antibody, and that the degree of substitution required to achieve this result does not unreasonably diminish the turnover rate for the enzyme, nor substantially change the enzyme's solubility characteristics.

In choosing an enzyme for commercialization, as compared to single or limited use for scientific investigation, there will be a number of desirable criteria. These criteria may be found in U.S. Pat. No. 3,817,837.

Particularly useful enzymes are the oxidoreductases and the hydrolases. When A is an oxidoreductase, it will generally be a dehydrogenase, more usually a dehydrogenase dependent on nicotinamide adenine dinucleotide (NAD) or its phosphate, (NADP), and even more usually a dehydrogenase also dependent on a CHOH substrate. More specifically, the enzyme may be malate dehydrogenase or glucose-6-phosphate dehydrogenase (G6PDH). Hydrolases of particular interest include lysozyme or alkaline phospatase.

While various sources of G6PDH may be employed, a particularly desirable source for the subject compounds is the bacterium L.mesenteroides which uses NAD.

In preparing the enzyme conjugates, it is desireable that at least 20, preferably at least 40 and particularly preferred at least 50% of the original enzyme activity be retained by the enzyme conjugate. Furthermore, the enzyme should be substituted in such a manner that when one or more groups are bonded to the enzyme, and are bound by antibody, the activity of the enzyme-conjugate is reduced by at least 30% of its original activity after conjugation, usually by at least 40%, and preferably by at least 50%.

In preparing the subject composition, the following reaction scheme provides an effective method for preparing the desired poly(amino acid) conjugates.

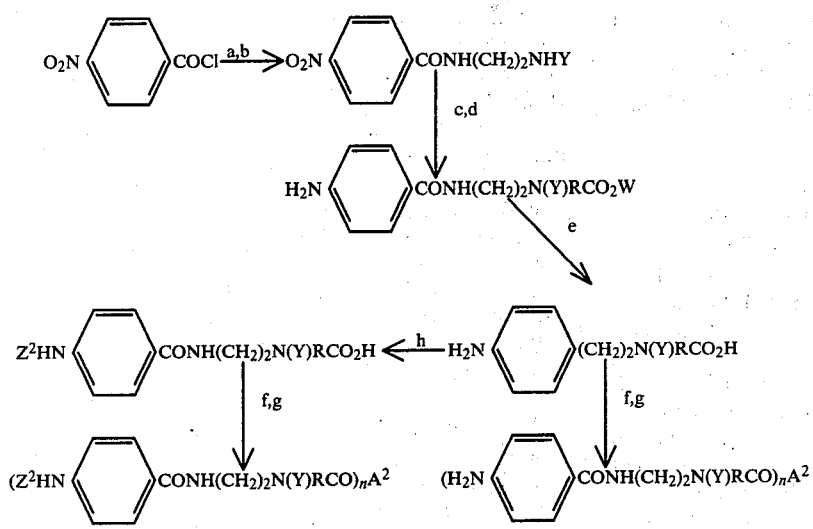

$A^2$ is a poly(amino acid) that is antigenic or an enzyme.
R,Y, and n have been defined previously.
W is lower alkyl of from 1 to 6, usually 1 to 3 carbon atoms.
$Z^2$ is acetyl.
 (a) MeOH
 (b) $NH_2(CH_2)_2NH(Y)$
 (c) $BrCH_2CH=CHCO_2W$ (where R is trimethylene)
 (d) $H_2$, Pd—C
 (e) MeOH, NaOH
 (f) N-hydroxy succinimide and N,N'-dicyclohexyl carbodiimide
 (g) $A^2H$
 (h) AcCl In forming the final product, the carboxylic acid precursor will normally be activated as described previously to form an amide or amidine link.

The antibodies which are prepared in response to the conjugated antigens made in the above manner are produced in high titer, and have strong specific binding to the parent drug as well as the enzyme conjugates used for the immunoassay.

EXPERIMENTAL (The following examples are offered by way of illustration and not by way of limitation. All temperatures not indicated are in Centigrade.)

EXAMPLE I

Preparation of N-(N'-ethyl 2-aminoethyl) p-nitrobenzamide

A. With strong stirring, 75 g of p-nitrobenzoyl chloride was added to 300 ml of absolute methanol in small batches; the solution became warm, cleared, and then formed a precipitate. After complete addition, the solution was boiled for 30 min. and filtered. The product crystallized from the cooling solution. The product was collected to give 47.5 g of light yellow crystals, m.p. 90°–92.5°. Concentration of the methanol solution gave a second crop, 25 g, m.p. 89°–92°, for a total of 72.5 g, 99%.

B. A solution of 5 g of N-ethyl ethylenediamine and 10.6 g of methyl p-nitrobenzoate (56.8 mmole each) in 40 ml of toluene was refluxed for 14 hours. The solvent was evaporated and the residue was dissolved in 200 ml of cold, dilute HCl, which was extracted with 200 ml of methylene chloride, from which 1.6 g of ester was recovered.

The aqueous layer was cooled, the pH adjusted to 10 with NaOH pellets, and the layer extracted thrice with 600 ml total of methylene chloride, which was washed with brine, dried and evaporated to give 11.37 g of a yellow solid (96%, based on recovered ester). The product was crystallized from ethyl acetate-cyclohexane, m.p. 83°–85°.

EXAMPLE II

Preparation of N-(N'-ethyl, N'-(3'-carbethoxy-2'-propenyl-1') 2-aminoethyl) p-nitrobenzamide Under nitrogen, 15.8 g of the amine prepared above and 12.9 g of distilled ethyl 4-bromocrotonate (67 mmoles each) in 150 ml of dry DMF was stirred at ambient temperature for 2 hrs; tlc at 0.5 and 2 hrs showed ca 50% reaction. Anhydrous sodium carbonate (16 g) was added; after 2 hrs, the reaction was complete.

The DMF was removed in vacuo and the residue swirled with chloroform filtered (with several chloroform washes), combined (600 ml total), washed with brine, dried and evaporated to give 33.4 g of a brown oil, which contained the product and DMF. The oil was chromatographed on 200 g of BioRad Ag-7 alumina, activity II, with neat methylene chloride. Tubes containing product were pooled to give 20.7 g of product, ca 98% pure by tlc.

EXAMPLE III

Preparation of N-(N'-ethyl,N'-(3'-carbethoxypropyl-1') 2-aminoethyl) p-aminobenzamide In 100 ml of absolute ethanol, 8.35 g of the compound of Example II was hydrogenated over 2 spatulas-full of 10% Pd/C in a Parr apparatus at ca 40 lbs/in$^2$ for 3-4 hrs. Under a nitrogen blanket, the catalyst was filtered off through a Celite pad (sintered glass funnel), which was washed with two volumes of ethanol. Evaporation gave ca 7.2 g of a brown oil.

The product was purified with a short column on 750 g of Merck GF silica eluted with 2% methanol-chloroform; the product (ca 7 g) eluted clearly and last from the column. The product is very hygroscopic and decomposes on long standing. In practice, the compound was purified by preparative tlc (silica, 5% methanol-chloroform+1% conc. NH$_4$OH) immediately before use.

EXAMPLE IV

Preparation of N-(N'-ethyl,N'-(3'-carboxypropyl-1') 2-aminoethyl) p-aminobenzamide The ester (Example III) was saponified by dissolving 2.48 g, (773 mmoles) in 20 ml of methanol and 10 ml of 1 N sodium hydroxide and stirring at ambient temperature overnight. The solution was concentrated in vacuo, neutralized and evaporated to a foam. The product was separated from salt by continually dissolving the foam in absolute methanol and evaporating until no methanol-soluble material remained. The sodium salt was isolated as a foam by dissolving the neutral product in an equivalent of 1 N sodium hydroxide and evaporating (ca 2.2 g, 91%).

EXAMPLE V

Acetylation of N-(N'-ethyl,N'-(3'-carboxypropyl-1') 2-aminoethyl) p-aminobenzamide To a stirring solution under nitrogen of 200 mg (0.682 mmol) of the acid of Example IV and 2 ml dry DMF at −15° was added dropwise with a microsyringe 53 μl (0.682 mmol) of acetyl chloride. The reaction was monitored by tlc analysis, silica gel GF-methanol. After 1 hr the reaction was complete, 20 ml water was added, the mixture neutralized with NH$_4$OH, followed by evaporation on a rotor evaporator and drying in vacuo.

Chromatography (prep tlc silica gel PF-254, eluant absolute methanol) of the product, followed by extraction of the appropriate band with methanol, and solvent evaporation yielded 192 mg (80%), crystallized from ethyl acetate-methanol m.p. 111°–113°.

EXAMPLE VI

Conjugation of bovine serum albumin or bovine gamma globulin (BSA or BgG) and N-(N'-ethyl, N'-(3'-carboxypropyl-1') 2-aminoethyl) p-aminobenzamide A. Conjugation to BSA To a stirring solution of 300 mg (1.023 mmol) of dry product of Example IV (as the acid) and 120 mg (1.023 mmol) of N-hydroxy succinimide (NHS) in 3 ml anhydrous DMF at 0° was added 231 mg (1.023 mmol) of dicyclohexylcarbodiimide. The reaction flask was equipped with calcium chloride drying tube and kept at 5° for 26 hrs.

The above reaction mixture was passed through a glass wool filter into a stirring solution of 1gm of Miles BSA dissolved in 40 ml of Na$_2$CO$_3$-NaHCO$_3$ buffer pH 9.6 at 0°. The reaction vessel was rinsed with 2 ml of DMF and added to the protein solution, which became turbid upon complete addition. The conjugate mixture was stirred at 0° overnight (16 hrs).

The conjugate was diluted with 50 ml buffer to a total volume of 90 ml, divided in two dialysis cylinders (mw. cutoff 6,000–8,000; cyl. dia. 14.6 mm) and dialyzed against 2 liters of H$_2$O-NH$_4$OH, pH 9.4 four times.

The solution was centrifuged 10,000 RPM for 15 min. and passed through 0.22 μm millipore filter, lyophilization in a sterilized flask gave ca 650 mg of conjugate.

The hapten number was determined by uv difference technique to be 16 at λmax 274. The hapten number was not changed by passing the conjugate through a Sephadex G50 column.

B. Conjugation to BgG

The reaction mixture composed of 153 mg (5.22 mmol) of dry Example IV (as the acid), 90 mg (7.83 mmol) of N-hydroxy succinimide and 103 mg (5.22 mmol) of dicyclohexylcarbodiimide in 3 ml anhydrous DMF was stirred at 0°–5° for 24 hrs. Within a few hours a white precipitate formed.

The solution of NHS-ester was added dropwise through a glass wool filter into a stirring solution of 0.5 g BgG in 30 ml NaCO$_3$-NaHCO$_3$, pH 9.8 buffer at 0°. The reaction vessel was stored in a cold room overnight 0°–5°.

The resulting solution which was slightly turbid was placed in a dialysis cylinder (mw cutoff 6,000–8,000; cyl. dia. 14.6 mm) and dialyzed against 2 liters of H$_2$O-NH$_4$OH pH 9.8 four times.

The solution was centrifuged for 30 min at 10,000 RPM and passed through a 0.22 μm millipore filter. Lyophilization in a sterilized flask gave ca 450 mg of conjugate. UV analysis showed a hapten number of 11.

In order to increase the hapten number the above procedure was repeated with the conjugate. The hapten number was then found to be 24.

EXAMPLE VII

Conjugation of N-(N'-ethyl, N'-(3'-carboxypropyl-1') 2-aminoethyl) p-acetylaminobenzamide to BgG and BSA A. Conjugation to BgG To a stirring solution of 350 mg (1.00 mmol) of dried product of Example V, 120 mg (1.00 mmol) N-hydroxy succinimide and 3 ml dry DMF at 0° was added 206 mg (1 mmol) of dicyclohexylcarbodiimide. The reaction vessel was equipped with a CaCl$_2$ drying tube and placed in a cold room 0°–5° for 40 hours.

To a vigorously stirred solution of 1 g BgG (Miles-Lot 57) in 80 ml of Na$_2$CO$_3$—NaHCO$_3$ buffer pH 9.8 at 0° was added dropwise the reaction mixture, after passing through glass wool filter to remove precipitated cyclohexylurea. The conjugation solution was kept at ca 5° overnight.

The conjugate was divided into two dialysis cylinders and subjected to successive changes; first 4 liter Na$_2$CO$_3$—NaHCO$_3$ buffer, pH 9.6, 4 hours; 4 liter NH$_4$OH-H$_2$O, pH 9.6, 4 hrs; 6 liter NH$_4$OH—H$_2$O, pH 9.6, 2 days.

The solution was centrifuged for 10 min at 10,000 RPM, lyophilized, and UV analysis showed a hapten number of 11.

The conjugate hapten number was increased by repeating the above procedure, and the solution then passed through 0.22 μm millipore filter. Lyophilization of the product in a sterile flask gave a conjugate with a hapten number of 21.

B. Conjugation to BSA

In a dry 10 ml round bottom flask was placed 156 mg (4.68 mmol) of dried product of Example V, 91 mg (4.68 mmol) of dicyclohexylcarbodiimide, 69 mg (10% excess) N-hydroxy succinimide and 2 ml anhydrous DMF under nitrogen atmosphere. The reaction mixture was stirred at room temperature for 4 hrs, during which time a precipitate formed. The mixture was then placed in a cold room at 0°–5° for an additional 22 hrs. The solution of NHS-ester was passed through a glass wool filter and the resulting filtrate added dropwise to a stirring solution of 500 mg (0.0078 mmol) of BSA and 40 ml of $Na_2CO_3$-$NaHCO_3$ buffer, pH 9.6 at 0°–5°. The reaction vessel was rinsed with 2 ml DMF and the rinse solution added to the protein solution. The conjugation mixture was stirred in a cold room at 0°–5° over the weekend. The solution of the conjugate was placed in a dialysis cylinder and treated against successive solvent changes; twice 6 liters $NH_4OH$-$H_2O$, pH 9.8, 4 hours each; once 6 liter $NH_4OH$-$H_2O$, pH 9.8 overnight.

The conjugate mixture was centrifuged for 15 minutes at 10,000 RPM, passed through a 0.22 μm millipore filter into a sterilized lyophilization flask (300 ml) to give 450 mg of the products with hapten number determined by UV ($\lambda 265$) of 11. Reconjugation of the product employed the following amounts of reagents: 450 mg conjugate, 136 mg Example V, 84 mg dicyclohexylcarbodiimide, 47 mg NHS, 2 ml dry DMF.

The increased hapten number was found to be 19, sample weight 370 mg.

EXAMPLE VIII

Conjugation of Glucose-6-phosphate dehydrogenase (G6PDH) and N-(N'-ethyl, N'-(3'-carboxypropyl-1') 2-aminoethyl) p-aminobenzamide.

The following compounds were combined and stirred at 4° overnight to form the NHS-ester: the product of Example IV (as the acid), 0.2 mM, 58.7 mg; N-hydroxy succinimide 0.2 mM, 23.0 mg; ethyl dimethylaminopropyl carbodiimide (EDAC) 0.23 mM, 44.1 mg; DMF, 1.0 ml. The pH was adjusted to 9.0 with 2N NaOH.

The following components were combined in the order shown at a temperature of 0°–4° C.: G6PDH, 10.0 ml of a ca 2 mg/ml solution in 0.055 M Tris-HCl buffer; Glucose-6-phosphate disodium salt, 200 mg; NADH 300 mg; Carbitol, 3.0 ml.

With the enzyme at 4° and the NHS-ester at room temperature, the NHS-ester was added to the enzyme in 10 μl amounts till a total of 580 μl NHS-ester had been added. The final pH was 8.5; the pH was allowed to drift.

The percent deactivation of the enzyme when conjugated and the percent inhibition of the conjugate in the presence of a saturating amount of antibodies were found to be 60% and 95%, respectively.

The conjugate was then dialyzed against a basic buffer composed of 0.055 M Tris-HCl, 0.05% sodium azide and 0.005% Thimerosal, pH 8.1.

EXAMPLE IX

Conjugation of G6PDH and N-(N'-ethyl,N'-(3'-carboxypropyl-1') 2-aminoethyl) p-acetylaminobenzamide The following compounds were combined and stirred at 4° overnight to form the NHS-ester: the product of Example V, 0.24 mM, 80.91 mg; N-hydroxy succinimide, 0.24 mM, 28.0 mg; EDAC, 0.278 mM, 53.3 mg; DMF 1.2 ml, with the pH adjusted to 9.0 with 2N NaOH.

The following components were combined at a temperature between 0°–4°: G6PDH, 10.0 ml of ca. 2 mg/ml solution suspended in 0.055 M Tris-HCl buffer; Glucose-6-phosphate disodium salt, 100 mg; NADH, 200 mg; Carbitol, 3.0 ml.

With both the enzyme and NHS-ester at 4° the NHS-ester was added in 101 μl amounts over a 3 hr period. A total of 750 μl NHS-ester was added. The pH was allowed to drift with the final pH at 8.5. The resulting deactivation was 57% and inhibition was 93%.

The conjugate was dialyzed against the same basic buffer as in Example VIII in a ratio of at least 1:500 through 7 changes of buffer over a 4 day time span.

Antibodies were prepared employing the conjugates of Example VI & VII in accordance with known procedures. The bleeds were harvested and the antibodies isolated according to known techniques.

The following is the assay procedure employed for the determination of the presence of procainamide and N-acetyl procainamide.

In carrying out the procainamide assay, a number of reagent solutions are prepared:

Basic Buffer
  0.055 M Tris-HCl
  0.05% Sodium Azide
  0.005% Thimerosal
  pH 8.1 at room temperature
Assay Buffer
  Basic Buffer +
  0.5% NaCl
  0.01% Triton X-100
  pH 8.1 at room temperature
Substrate/Antibody Diluent
  Basic Buffer +
  1.0% RSA (Rabbit Serum Albumin)
  0.04 M NAD in $H_2O$
  0.066 M glucose-6-phosphate
  pH 5.0 at room temperature
Enzyme Diluent
  Basic Buffer +
  1.0% RSA
  0.9% NaCl
  pH 8.1 at room temperature
Antibody-Substrate Reagent A
  Antibody-Substrate is used to dilute gamma globulin isolated as above using the conjugate formed in Example VI, so that ca. 86% of the G6PDH conjugate activity was inhibited in the assay solution.
  This reagent is then spiked with N-acetyl procainamide to a concentration of 10 μg/ml in order to depress the cross-reactivity with N-acetyl procainamide.
Enzyme Reagent B
  The enzyme conjugate (Example VIII) is diluted with enzyme diluent to attain the desired maximum rate. This is measured by aspirating into a spectrometer and taking the change in readings at 340 nm over a 30 second period after a 15 second delay.

In carrying out the assay, the assay solution is prepared by combining the following: 50 μl of the sample to be assayed, 50 μl of Reagent A, and 50 μl of Reagent B with 750 μl of assay buffer. The mixture is aspirated into the spectrometer and the ΔOD read at 340 nm. The concentration of procainamide in the sample is read from a standard curve prepared by using standardized solutions and taking readings.

The drugs in the following table were tested for cross-reactivity.

| | CROSS-REACTIVITY | |
|---|---|---|
| | Highest Level Tested (μg/ml) | Concentration Necessary To Elevate The Signal of a 4μg/ml Standard to 5.2μg/ml (μg/ml) |
| N-acetyl procainamide (NAPA) | 1000 | 400 |
| Quinidine | 100 | — |
| Propranolol | 100 | — |
| N-[2-(Diethylamino)ethyl]-4-pyridine carboxamide | 100 | 15 |
| Lidocaine | 100 | — |
| Digoxin | 1 | — |

It is apparent from this data that for practical uses, the assay is highly selective for procainamide. Therapeutic ranges of N-acetyl procainamide are at 4–8 μg/ml, far below the level at which N-acetyl procainamide shows interference with the procainamide assay. N-[2-(diethylamino)ethyl]-4-pyridine carboximide is only rarely used as an antiarrhythmic. The other antiarrhythmic drugs tested show no interference with the procainamide assay. Furthermore, various patient samples tests show positive correlation with the standard colorimetric method.

Additionally, the procainamide assay shows excellent reproducibility and precision. Reproducibility of a single spike was determined by pooling 14 individual samples and spiking at 4.0 μg/ml procainamide. Ten separate dilutions were made, and each dilution assayed in duplicate; the coefficient of variation of the 20 unaveraged duplicates was 2.1%.

Sample to sample variability was determined by spiking 25 individual samples at each of 1, 4, and 16 μg/ml. A maximum coefficient of variation of 4% was found when the assay results for the 25 samples at each concentration level were pooled, each sample being assayed in duplicate and the duplicates averaged.

The N-acetyl procainamide assay method is almost identical to the procainamide assay method. The enzyme, though, is conjugated with N-acetyl procainamide rather than procainamide, and the antibody Reagent B is spiked with procainamide, rather than N-acetyl procainamide to a concentration equivalent to 8 μg/ml in the sample.

This assay method exhibits high selectivity for N-acetyl procainamide. Cross-reactivity studies have shown no interference at the concentration ranges of interest with procainamide, p-acetamidobenzoic acid (a metabolite), acetaminophen, or N-acetyl sulfanilylurea.

This assay method, too, shows excellent reproducibility and precision. 20 replicate assays each of a standard solution at 1 μg/ml, 4 μg/ml and 16 μg/ml, as well as of sample solutions at approximately the same concentrations showed a maximum coefficient of variation of 6.9%. Sample-to-sample variability determined by spiking 10 samples each at 0.99 μg/ml, 3.98 μg/ml and 15.95 μg/ml, and making 20 determinations at each concentration, each determination an unaveraged duplicate of a spiked sample, showed a maximum coefficient of variation of 7.0%.

The foregoing data illustrates that the compounds of the subject invention are particularly effective in providing reagents which are useful in immunoassays for the determination of the benzamides of N, N-dialkylethyleneamines, particularly procainamide and N-acetyl procainamide. In addition, the antibodies which are provided are able to detect the presence of the benzamides of the N, N-dialkylethyleneamines, especially procainamide and N-acetylprocainamide in the blood. Thus, high specificity is achieved for a narrow class of compounds so the subject assay can be used to provide a rapid determination of the concentration of these compounds in the blood. The subject assays in conjunction with the antibodies prepared in accordance with this invention provide the ability to accurately and independently determine procainamide or N-acetyl procainamide. This permits quantitatively distinguishing between procainamide and its N-acetyl metabolite. This can be very important where the patient's respone to the drug may be substantially different.

The subject benzamides of N, N-dialkylethyleneamines are for the most part difficult to conjugate. The problems of preparing appropriate conjugates which may be used for the production of antibodies are overcome by employing the compounds of the subject invention. The antibodies produced using the conjugated antigens of the subject invention are at high concentrations and are found to provide the desired high binding constants for the individual compounds.

Although the foregoing invention has been described in some detail by way of illustration and example for purposes of clarity and understanding, it will be obvious that certain changes and modifications may be practiced within the scope of the appended claims.

What is claimed is:

1. A compound of the formula:

wherein:
Z is hydrogen or acetyl;
Y is alkyl of from 1 to 3 carbon atoms;
X is oxygen or imino (NH);
R is a linking of group of from 1 to 8 carbon atoms having from 0 to 4 heteroatoms, which are oxygen, nitrogen and sulfur, wherein the oxygen is present as oxy or nonoxocarbonyl, nitrogen is present as tertiary amino, amido or imino and sulfur is present as thioether or thiono, and having from 0 to 1 site of ethylenic unsaturation as the only unsaturation;
A is a poly(amino acid) which is antigenic or an enzyme;
n is 1 to the molecular weight of A divided by 1000.

2. A compound according to claim 1 wherein A is a poly(amino acid) which is antigenic.

3. A compound according to claim 1 wherein A is a poly(amino acid) which is an enzyme, and n is 1 to 30.

4. A compound according to claim 3 wherein said enzyme is an oxidoreductase or a hydrolase.

5. A compound according to claim 3 wherein said enzyme is glucose-6-phosphate dehydrogenase.

6. A compound of the formula:

wherein:
$Z^1$ is hydrogen or acetyl;
$R^1$ is alkylene of from 1 to 4 carbon atoms;
$A^1$ is a poly(amino acid) which is antigenic or an enzyme;
$n^1$ is 1 to the molecular weight of $A^1$ divided by 1000.

7. A compound according to claim 6 wherein $A^1$ is a poly(amino acid) which is antigenic.

8. A compound according to claim 6 wherein $A^1$ is an enzyme, said enzyme being glucose-6-phosphate dehydrogenase,
and $n^1$ is 1 to 30.

9. A compound of the formula:

wherein:
$Z^2$ is hydrogen or acetyl;
$A^2$ is bovine serum albumin or bovine gamma globulin;
$n^2$ is 1 to the molecular weight of $A^2$ divided by 1000.

10. A compound of the formula:

wherein:
$Z^3$ is hydrogen or acetyl;
$A^3$ is glucose-6-phosphate dehydrogenase;
$n^3$ is 1 to 30.

11. An antibody composition prepared in immunological response to procainamide or N-acetyl procainamide conjugated to an antigen through the amino group of the aminoalkyl bonded to the nitrogen of the benzamide group of procainamide, said antibody being capable of binding to procainamide and an enzyme conjugate according to claim 4, wherein Z is hydrogen, or N-acetyl-procainamide and an enzyme conjugate according to claim 4, wherein Z is acetyl.

12. An antibody composition prepared in immunological response to procainamide or N-acetyl procainamide conjugated to an antigen through the amino group of the aminoalkyl bonded to the nitrogen of the benzamide group of procainamide, and said antibody capable of binding to procainamide and an enzyme conjugate according to claim 10, wherein $Z^3$ is hydrogen, or N-acetyl-procainamide and an enzyme conjugate according to claim 10, wherein $Z^3$ is acetyl.

* * * * *